(12) United States Patent
Leblond et al.

(10) Patent No.: US 8,834,867 B2
(45) Date of Patent: *Sep. 16, 2014

(54) **METHOD FOR PRODUCING LIPASE, TRANSFORMED *YARROWIA LIPOLYTICA* CELL CAPABLE OF PRODUCING SAID LIPASE AND THEIR USES**

(75) Inventors: Yves Leblond, Orgeval (FR); Nicolas Mouz, St. Paul de Varces (FR); Alain Marty, Toulouse (FR); Jean-Louis Uribelarrea, Toulouse (FR)

(73) Assignee: Laboratoires Mayoly Spindler, Chatou (FR)

( * ) Notice: Subject to any disclaimer, the term of this patent is extended or adjusted under 35 U.S.C. 154(b) by 32 days.

This patent is subject to a terminal disclaimer.

(21) Appl. No.: 13/571,869

(22) Filed: Aug. 10, 2012

(65) Prior Publication Data

US 2013/0052180 A1 Feb. 28, 2013

Related U.S. Application Data

(62) Division of application No. 12/304,822, filed as application No. PCT/FR2006/001352 on Jun. 15, 2006, now Pat. No. 8,334,130.

(51) Int. Cl.
| | |
|---|---|
| *A61K 38/46* | (2006.01) |
| *C12N 1/00* | (2006.01) |
| *C12N 9/20* | (2006.01) |
| *C12Q 1/34* | (2006.01) |
| *C12P 21/06* | (2006.01) |
| *C12N 15/00* | (2006.01) |
| *C07H 21/04* | (2006.01) |
| *A61K 38/00* | (2006.01) |

(52) U.S. Cl.
CPC . *C12N 9/20* (2013.01); *A61K 38/00* (2013.01); *C12Y 301/01003* (2013.01)
USPC ......... 424/94.6; 435/254.2; 435/18; 435/198; 435/69.1; 435/320.1; 536/23.2

(58) Field of Classification Search
None
See application file for complete search history.

(56) References Cited

FOREIGN PATENT DOCUMENTS

| | | |
|---|---|---|
| WO | WO 01/83773 | 11/2001 |
| WO | WO 2006/039541 | 4/2006 |

OTHER PUBLICATIONS

F. Alonso, et al., "Improvement of Lipase Production At Different Stirring Speeds and Oxygen Levels", Brazilian Journal of Chemical Engineering, vol. 22, No. 1, pp. 9-18 (2005).
P. Fickers, et al., "Methyl Oleate Modulates L1P2 Expression in the Lipolytic Yeast *Yarrowia lipolytica*", Biotechnology Letters, vol. 27, No. 22, pp. 1751-1754 (2005).
M. Camargo-De-Morais et al. "Oil/mineral-salts medium designed for easy recovery of extracellular lipase from *Fusarium oxysporum* AM3", World Journal of Microbiology & Biotechnology 19: pp. 17-20, 2003.

*Primary Examiner* — Iqbal H Chowdhury
(74) *Attorney, Agent, or Firm* — Oblon, Spivak, McClelland, Maier & Neustadt, L.L.P.

(57) ABSTRACT

Method for producing *Yarrowia lipolytica* acid-resistant recombinant lipase utilizing a culture medium without any products of animal origin or non-characterized mixtures such as tryptone, peptone or lactoserum, in addition to its uses. Recombinant strain of *Yarrow lipolytica* producing an excessive amount of lipase $Lip^2$ referred to as YL-LIP2-6C and filed with the Collection Nationale de Cultures de Microorganismes (C.N.C.M.) under number I 3542, on Dec. 15, 2005 and its uses.

4 Claims, 6 Drawing Sheets

METHOD FOR PRODUCING LIPASE, TRANSFORMED *YARROWIA LIPOLYTICA* CELL CAPABLE OF PRODUCING SAID LIPASE AND THEIR USES

This application is a Divisional of U.S. application Ser. No. 12/304,822, filed on Jul. 1, 2009, which is a 35 U.S.C. §371 National Stage patent application of International patent application PCT/FR06/01352, filed on une 15, 2006.

The present invention relates to a method for producing lipase using *Yarrowia lipolytica* yeast cells which produce an acid-resistant recombinant lipase, which method allows the production of a lipase capable of being used as a medicament; the present invention also relates to a *Yarrowia lipolytica* strain overproducing an acid-resistant recombinant lipase and its applications.

The foods ingested daily by humans consist mainly of lipids, proteins and sugars. All these constituents undergo, before their absorption, hydrolysis catalyzed by the enzymes of the digestive tract. A deficiency in any of these enzymes can therefore cause digestive disorders and lead to considerable malnutrition. That is for example the case in some pathological situations such as cystic fibrosis or exocrine pancreatic insufficiency, which are associated with a pancreatic lipase deficiency. To correct this deficiency, it is conventionally proposed to orally administer pancreatic extracts. However, the efficiency of this therapy is limited by the fact that the enzymes contained in these extracts (lipases, amylases and proteases) are rapidly inactivated by the acidity of the gastric medium.

It has therefore been proposed to use lipase preparations which are resistant to the gastric conditions, such as for example mammalian gastric lipase preparations produced by genetic engineering, such as that described in French patent application published under the number 2 699 179, in the name of INSTITUT DE RECHERCHE JOUVENIAL SA or microbial lipase preparations having reasonable activity in an acidic medium [ZENTLER-MONRO et al., Pancreas, 7, 311-319 (1992)].

Among microbial lipases that are active in acidic medium, there may be mentioned in particular fungal lipases, such as those from *Candida ernobii* [YOSHIDA et al., Biochim. Biophys. Acta.; 154, 586-588 (1968)], from *Trichosporon asteroid* [DHARMSTHITI et al., Biotechnol. Appl. Biochem., 26, 111-116 (1997)], from *Rhizopus javanicus* [UYTTENBROECK et al., Biol. Chem. Hoppe Seyler, 374, 245-254, (1993)], or from *Yarrowia lipolytica* [HADEBALL, Acta Biotechnol., 2, 159-167 (1991); NOVOTNY et al., J. Basic Microbiol. 28, 221-227 (1988)]. In addition to their activity at acidic pH, these lipases have the common characteristics of being resistant, in the presence of their substrate, to digestion by proteases (trypsin, chymotrypsin and pepsin), and of being resistant to the action of bile salts (their activity is preserved in the presence of 10 mM sodium taurocholate).

The use of *Yarrowia lipolytica* for the production of a gene of interest has already been described. Thus, application EP 1 108 043, in the names of INRA and CNRS, describes the use of an integrative vector comprising a cassette for expressing a gene of interest and zeta sequences, corresponding to the LTR sequences of the *Yarrowia lipolytica* Ylt retrotransposon. Such an expression vector allows the nonhomologous and dispersed integration of several copies of the insert of interest into the genomic DNA of a *Yarrowia lipolytica* strain lacking a zeta sequence. This system has in particular been used for the integration of the LIP2 gene, encoding a lipase, into the *Yarrowia lipolytica* DNA and has allowed, under culture conditions which are not detailed, secretion of lipase 10 to 15 times higher than that of nontransformed strains.

Other studies describe the use of the same expression vector as that described in patent application EP 1 108 043, for the production of a recombinant lipase in *Yarrowia lipolytica* (International application WO 01/83773; PIGNEDE et al., Journal of Bacteriology, vol. 182, No. 10, p. 2802-2810 (2000) and PIGNEDE et al., Applied and Environmental Microbiology, vol. 66, No. 8, p. 3283-3289 (2000)). Thus:

International application WO 01/83773, in the name of Laboratoires MAYOLY SPINDLER, describes the production of the *Yarrowia lipolytica* MS4 clone (CNCM I-2294), comprising 10 copies of the cassette for expression of the LIP2 gene that are integrated into its DNA, and its use for the production of lipase with a yield of the order of 0.5 g of lipase per liter of culture supernatant, and a catalytic activity of 12 000 U/ml, measured using olive oil as substrate, one unit corresponding to the quantity of enzyme capable of catalyzing the release of 1 µmol of fatty acid per minute, that is to say 200 times more than the initial strain. However, the method of producing lipase described in this application has a major disadvantage since it uses culture media containing bactopeptone or bactotryptone. These products, which are not characterized and which contain various protein hydrolysates, are conventionally used as nitrogen and carbon source. Consequently, the method described in this application does not make it possible to obtain a lipase that can be directly used as a medicament.

PIGNEDE et al. (Journal of Bacteriology, 2000) have more particularly characterized the extracellular lipase encoded by the *Yarrowia lipolytica* (POld strain) LIP2 gene. In this article the following are thus studied:

the secretion of lipase from various wild-type strains (POld from which Ylt1 is absent and E150 in which Ylt1 is present) and from various recombinant strains including JMY184 (POld-6-15) and JMY279 (POld-6-17), and the overproduction of lipase in particular by the transformant JMY184.

This article by PIGNEDE et al. compares the production of lipase by wild-type strains, mutant strains and recombinant strains obtained according to the method described above (International application WO 01/83773). The wild-type strains secrete between 30 and 50 U of lipase/ml while mutant strains obtained by the action of N-methyl-N'-nitro-N-nitrosoguanidine (NNNG) produce 25 times more lipase, that is to say 1200 U/ml under optimized culture conditions involving a medium containing peptone (preculture medium) and a medium containing whey (fermentation medium) (also see DESTAIN et al., 1997). The recombinant strains are obtained with the aid of the construct comprising the LIP2 gene regulated by the POX2 promoter and by the nonhomologous integration, in multicopies and in a dispersed manner, of this expression cassette. PIGNEDE et al. obtained stable transformants (for example the strain JMY184) which produce 2000 U/ml under nonoptimized conditions, that is to say in a YPDH medium (comprising 10 g/l of yeast extract, 10 g/l of bactopeptone, 10 g/l of glucose and 10 g/l of olive oil) corresponding to about 0.5 g of lipase/l of supernatant. In the same manner as above, the lipase preparations described by PIGNEDE et al. and by DESTAIN et al., are unsuitable, as such, for medical use and more particularly for the preparation of clinical batches, since their production requires the use of culture media containing peptones or whey.

Pursuing its work, the PIGNEDE team (Applied and Environmental Microbiology, 2000) studied *Yarrowia lipolytica* strains transformed with a vector comprising a cassette for expressing the LIP2 gene. The authors determined that for 8 of these transformants, the number of copies of the cassette for expression of the LIP2 gene is between 6 and 16 (10 copies on average), which results in 2 to 15 events for integration of said cassette at different loci. The JMY184 strain thus comprises 12 copies of the LIP2 gene expression cassette, integrated at 4 different loci. The authors moreover more specifically studied this JMY184 transformant. They confirm that the JMY184 strain produces 0.5 g of lipase/l of supernatant with an activity of 1500 U/ml on rich YPDH medium (which contains bactopeptone) (against 50 U/ml for a wild-type strain PO1d), measured using olive oil as substrate. These values make it possible to deduce a specific activity of about 3000 U/mg of lipase. The authors additionally announce that the optimized production of lipase in the fermenter by the JMY184 strain makes it possible to obtain preparations having an activity of up to 10 000 U/ml. However, the culture conditions which allowed this result are not disclosed. In this article, the authors additionally studied the stability of these transformants, and in particular of the JMY184 clone, in culture and showed their stability for 120 generations. PIGNEDE et al. considered that to optimize the production of lipase, the factors to be taken into account are the stability of the transformants and the culture conditions.

Moreover, they showed that there is a strong correlation between the number of copies of the LIP2 gene integrated and the overproduction of lipase.

However, for the production of lipase, the only culture media envisaged in this article are media which contain peptones, such as the rich YPDH medium.

The prior art methods of producing lipase, even though they make it possible to obtain improved yields of lipase, are not suitable for the production of a lipase suitable for use for medical purposes.

Indeed, the culture media usually used all contain uncharacterized mixtures and/or products of animal origin, such as peptones, tryptones or whey. A need therefore exists to develop a system allowing the production of preparations of recombinant lipase suitable for medical use.

To solve this problem, the inventors have developed a method for producing lipase which better meets these needs than the prior art methods of production. More specifically, the inventors have developed a method for producing lipase in which the culture medium used is free of the abovementioned products, that is to say that it contains no product of animal origin and no uncharacterized mixture such as peptone, tryptone or whey. The inventors have additionally selected a novel recombinant *Yarrowia lipolytica* strain producing the lipase Lip2, which, combined with said method, additionally makes it possible to significantly increase the yield of lipase produced.

The subject of the present invention is therefore a method for producing lipase using a *Yarrowia lipolytica* strain transformed by a vector comprising a cassette for expressing a yeast acid-resistant lipase, characterized in that the culture medium used does not contain products of animal origin or uncharacterized mixtures, such as peptone, tryptone or whey.

More specifically, the subject of the present invention is a method for producing lipase, comprising:

a) a step for culturing *Yarrowia lipolytica* cells transformed with an expression vector comprising a cassette for expressing a yeast acid-resistant lipase, under conditions allowing the production of lipase;

b) a step for recovering the lipase thus produced from the supernatant of said culture;

which method is characterized in that step a) for culturing is carried out in a culture medium free of products of animal origin or of uncharacterized mixtures consisting of protein materials of animal origin (whey for example) or of products of their enzymatic digestion (tryptone or peptone for example).

According to an advantageous embodiment of said method, said culture medium according to step a) comprises:

as nitrogen source, inorganic nitrogen, and preferably ammonium sulfate;

a carbon source selected from carbon sources of carbohydrate origin, polyalcohols such as glycerol, and carbon sources of lipid origin such as fatty acids and acylglycerols; and inorganic salts, trace elements and vitamins.

According to another advantageous embodiment of said method, step a) comprises:

a1) a step for preculturing the transformed *Yarrowia lipolytica* cells as defined above in a medium containing a carbon source of carbohydrate origin; and a2) a step for fermenting by said cells comprising a cell growth phase in a medium containing a carbon source of carbohydrate origin and a phase for synthesizing lipase in a medium containing, as sole carbon source, a fatty acid chosen from short-, medium- or long-chain triglycerides. Thus, the fermentation is carried out in a first instance so as to allow cell growth, for example in the presence of a carbon source of carbohydrate origin, and in a second instance under conditions allowing the biosynthesis of said lipase, for example in the presence, as sole carbon source, of a chemical inducer of the fatty acid type, such as a short-chain triglyceride (such as tributyrin), a medium-chain triglyceride (such as trioctanoin or trioctanoylglycerol) or a long-chain triglyceride (such as olive oil or triolein).

The fermentation is advantageously carried out with a constant pO2 of between 15% and 25% and a pH of preferably less than 6.5. The fermentation may for example be carried out with an air flow rate of about 1 vvm, one vvm unit being 1 volume of air per volume of liquid per minute (for example for a 30-liter fermenter, 1 vvm is equal to 30 l/min and for a 5-liter fermenter, 1 vvm is equal to 5 l/min).

According to an advantageous feature of this embodiment, step a1) for preculturing is carried out up to an $OD_{600nm}$ value of between 3 and 10 per 1 ml, and in step a2) for fermentation, said phase for synthesizing lipase is initiated when the $OD_{600nm}$ of the culture reaches a value between 60 and 70 per 1 ml.

According to another advantageous feature of this embodiment, step b) is initiated when the $OD_{600nm}$ reaches a value between 300 and 350 per ml. Step b) may additionally comprise:

b1) the separation of the lipase from said culture supernatant;

b2) the purification of the lipase obtained in b1).

These two steps are carried out by conventional techniques known per se: physical separation (filtration, chromatography, centrifugation) or physicochemical separation (precipitation).

The separation of the lipase from the supernatant may be carried out by a person skilled in the art, for example by a technique chosen from hollow fiber tangential filtration, frontal filtration and continuous or batch centrifugation.

The purification of the lipase consists in particular in reducing the bioload, that is to say the presence of microorganisms, and may be carried out by any suitable purification technique known to a person skilled in the art, such as a technique chosen from filtration, fractional precipitation, ion-exchange chromatography, hydrophobic interaction chromatography and gel-filtration chromatography.

Optionally, the method for producing lipase according to the invention may also comprise a concentration or enrichment step consisting of increasing the concentration of lipase in the preparation. Such a step may be carried out for example after the purification step. It may also take place simultaneously with this purification step.

The method of production according to the invention makes it possible in particular to produce recombinant lipase in quantities of between about 1 and 3 g of purified lipase per liter of culture supernatant. In a particularly advantageous manner, the method according to the invention allows the production of a recombinant lipase preparation with a catalytic activity greater than 15 000 U/ml of culture supernatant. Preferably, said preparation has an activity greater than 20 000 U/ml of culture supernatant. These values are determined at pH 6, using trioctanoin as substrate. This activity value for the lipase preparation is of most particular interest in the context of the development of pharmaceutical products. It is indeed now feasible to administer reduced doses of lipase, produced by the method according to the invention, while retaining sufficient efficacy to obtain the desired therapeutic effect, which may be for example the correction of a malabsorption of fat linked to pancreatic insufficiency associated with a lipase deficiency.

The fact that the lipase Lip2 can now be produced using recombinant *Yarrowia lipolytica* strains without requiring products of animal origin, as is the case with the method according to the invention, constitutes a considerable advantage and greatly facilitates the use of lipase for medical purposes.

The expression vector used to obtain the recombinant *Yarrowia lipolytica* cells used in the method of the present invention is an integrative vector having at least one copy of the LIP2 gene and elements for regulation of expression. This vector may then be integrated either into the plasmid DNA or into the genomic DNA of the yeast. One example of a particularly preferred integrative vector is the vector JMP6 or the vector JMP10 as described in International application WO 01/83773. The vector JMP6 comprises a cassette for expression of the LIP2 gene, encoding the Lip2p precursor of the *Yarrowia lipolytica* Lip2 lipase, upstream of which is placed the *Yarrowia lipolytica* promoter for acyl CoA oxidase ACO2, called POX2. The vector JMP10 also comprises the LIP2 gene, upstream of which is the *Yarrowia lipolytica* promoter for the Lip2 lipase. These two promoters are inducible by triglycerides and fatty acids. In each of these vectors, the expression cassette and the promoter are placed between the zeta sequences as described above. The integration may be targeted, that is to say directed at sites, or random. Thus, when the transformed *Yarrowia lipolytica* strain is free of zeta sequence (that is for example the case for the POld strain), the integration of the expression cassette is dispersed in the genomic DNA of said strain. On the other hand, when the *Yarrowia lipolytica* strain comprises zeta sequences (that is for example the case for the E150 strain), the integration is mainly directed at the level of these sequences.

According to another advantageous embodiment of said method, the transformed *Yarrowia lipolytica* strain is preferably the strain called YL-LIP2-6C, deposited at the Collection Nationale de Cultures de Microorganismes (C.N.C.M.), 28 rue du Docteur Roux, 75724 Paris Cedex 15, on 15 Dec. 2005, under the number I-3542. This YL-LIP2-6C strain is genetically stable.

For the purposes of the present invention, the expressions "stable", "genetically stable", "genetic stability", and variants thereof, are used with reference to the conservation of the same number of loci for integration of a nucleic acid of interest into the DNA of the clone considered, for at least 30 generations. This number of 30 generations is chosen as the basis for calculating genetic stability because the inventors observed that it corresponds to a number of doublings of the cell population sufficient to allow the production of lipase using a method comprising at least one step for preculturing recombinant *Yarrowia lipolytica* cells and one step for producing lipase proper under fermentation conditions. For the purposes of the present invention, a generation is defined by the doubling of the cell population and may be calculated according to the formula $Y=X*2^g$ where Y is the cell population at time t (for example expressed as cell density), X is the initial cell population at time $t_0$ and g represents the number of generations necessary for the cell population to pass from the value X to the value Y. Preferably, the clone is said to be genetically stable when at least 90% of the colonies analyzed, after at least 30 generations, contain the same number of loci of the gene of interest as the starting clone. Thus, as is evident from the examples, the clone YL-LIP2-6C is said to be stable because nearly 100% of the colonies analyzed after 100 generations contain 6 loci of the LIP2 gene (one locus corresponding to the endogenous LIP2 gene+5 loci for integration of the cassette for expression of the LIP2 gene).

Surprisingly, when the method according to the invention uses this particular strain, the inventors succeeded in producing recombinant lipase in a large quantity and in having a better control over said production. The inventors indeed succeeded in improving the yield of production of lipase and in particular were able to obtain a production of the order of 1 to 3 g of pure lipase per liter of culture supernatant. They were also able to obtain lipase preparations having an activity close to 20 000 U/ml.

For the purposes of the present invention, the activity of the lipase corresponds to its enzymatic activity. The catalytic activity of a solution of lipase is expressed as unit (U) per ml of solution analyzed. The specific activity is expressed as unit (U) per mg of purified protein (lipase). One unit corresponds to the quantity of enzyme capable of catalyzing the release of 1 µmol of fatty acid per minute. The specific activity of a lipase varies according to the nature of the triglyceride used as substrate.

In addition to the improvement in the yield of production of the lipase, the inventors were also able to provide a better reproducibility of the method of production, improve the homogeneity of the final product and improve the conditions for purifying the lipase.

These various modifications therefore make it possible to obtain a lipase satisfying the conditions required for a medical use. Indeed, in the context of their research, the inventors have now observed that the Lip2 lipase is active at pH values greater than 3 and up to a pH value close to 8, with an optimum activity for a pH between 5 and 6. On the other hand, it is irreversibly inactivated during a 2-hour incubation at pH 3 or pH 8.5. The specific activity of the Lip2 lipase was also analyzed as a function of various substrates and the inventors thus determined at pH 4 the values of about 10 760 U/mg, about 16 920 U/mg and about 12 260 U/mg of purified lipase, with short-chain triglycerides (tributyrin), medium-chain triglycerides (trioctanoin) and long-chain triglycerides (olive oil), respectively. Finally, the inventors observed surprisingly that the Lip2 lipase is active in the presence of bile salts and that this activity increases with the concentration of bile salts. This activity in the presence of bile salts had up until now only been observed with gastric lipase and pancreatic lipase combined with the co-lipase. Thus, the use of Lip2 lipase with a high specific activity does not require the presence of a co-lipase.

The clone YL-LIP2-6C contains several copies of the cassette for expressing this Lip2 lipase resulting in 5 events for integration of the LIP2 gene at various loci. When it is placed under conditions suitable for the production of lipase, the clone YL-LIP2-6C produces more lipase than the transformed *Yarrowia lipolytica* strains of the prior art. The lipase is produced in a yield greater than 1 g/l of culture supernatant, that is to say greater than the yield observed with the prior art clones described above.

The subject of the present invention is also a lipase preparation which can be obtained by the method according to the invention.

According to an advantageous embodiment of said lipase preparation, it has an activity at least equal to 15 000 U/ml, preferably greater than 20 000 U/ml when it is determined as indicated above.

The subject of the invention is additionally the use of the lipase preparation according to the invention for the preparation of a medicament intended for the treatment of a pathology associated with a disruption of the absorption of fat (for example short-, medium- or long-chain fatty acids), in particular linked to a pancreatic insufficiency, in particular exocrine pancreatic insufficiency.

The subject of the invention is also a medicament, characterized in that it comprises a lipase preparation as defined above.

The subject of the present invention is also a *Yarrowia lipolytica* cell transformed by a vector for expressing a yeast acid-resistant lipase, characterized in that it is the clone called YL-LIP2-6C, deposited at the Collection Nationale de Cultures de Microorganismes (C.N.C.M.), 28 rue du Docteur Roux, 75724 Paris Cedex 15, 15 Dec. 2005 under the number I-3542.

The subject of the present invention is additionally the use of a cell as defined above for the production of yeast acid-resistant lipase.

In addition to the preceding features, the invention also comprises other features, which will emerge from the description which follows, which refers to examples of carrying out the method which is the subject of the present invention and to the accompanying drawings, in which.

Figure 3:
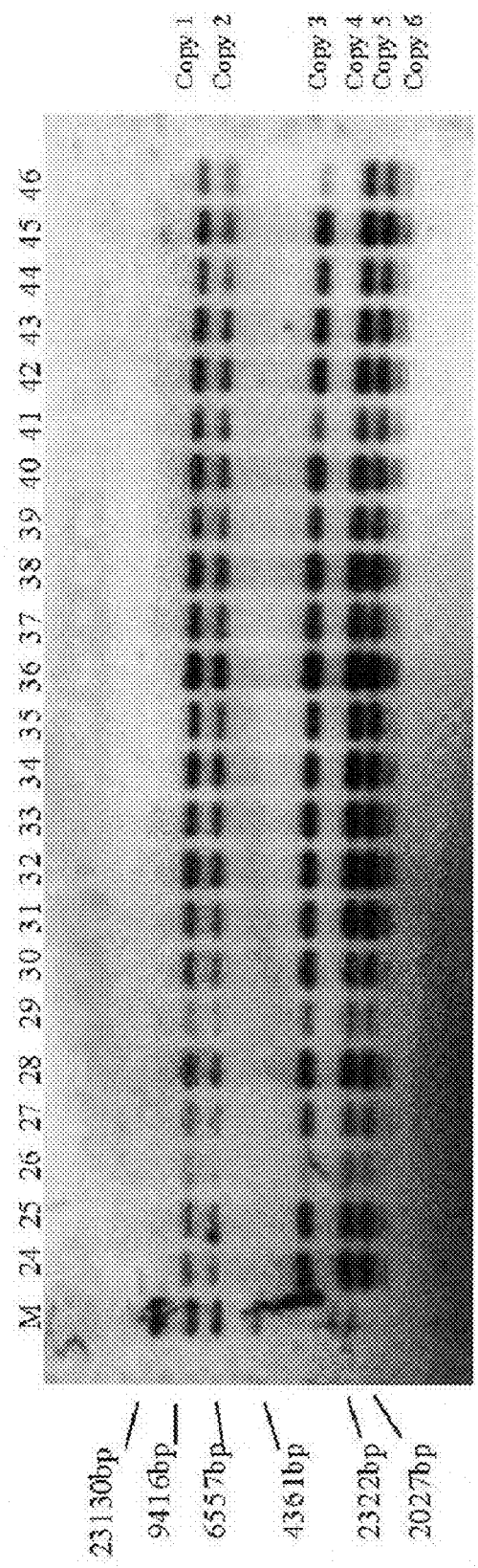

FIG. 3 represents the Southern blot analysis of the number of events for integration of the LIP2 gene at different loci into the genome of 23 colonies (lanes 24 to 43) collected at time T33, corresponding to the end of the fermentation, about 100 hours after the start of the fermentation. Copies 1 to 6: 6 loci of the LIP2 gene (5 loci for the integration of the cassette for expression of the LIP2 gene+one locus for the endogenous LIP2 gene). M: size marker.

Figure 4:
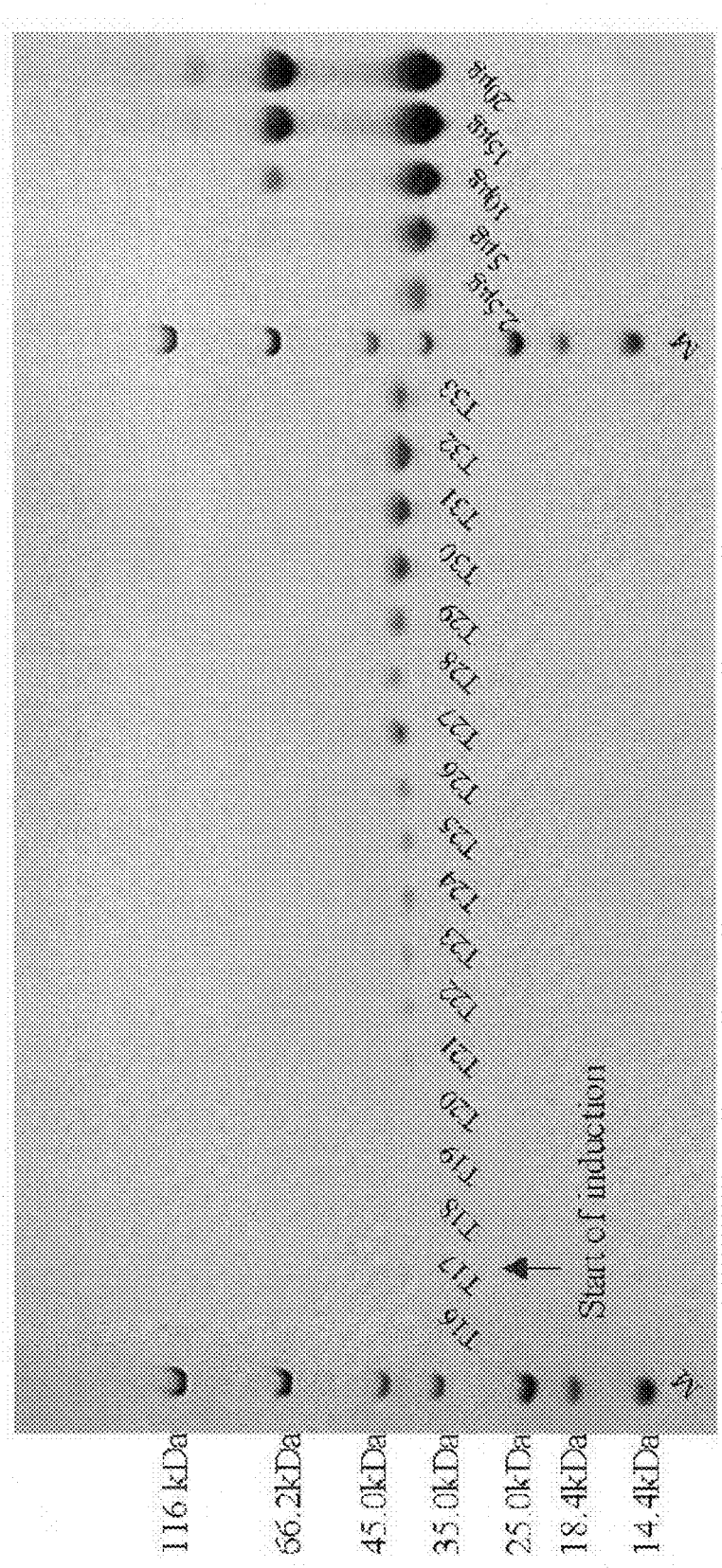

FIG. 4 represents the monitoring, by SDS-PAGE, of the production of recombinant lipase by the YL-LIP2-6C clone during the method of production, from T16 to T33. The arrow indicates the induction of the production of lipase (T17, 48 hours of fermentation). M: molecular weight ladder; the five lanes of the right hand part of the gel correspond to known quantities (2.5 μg to 20 μg) of purified Lip2 lipase.

Figure 5:
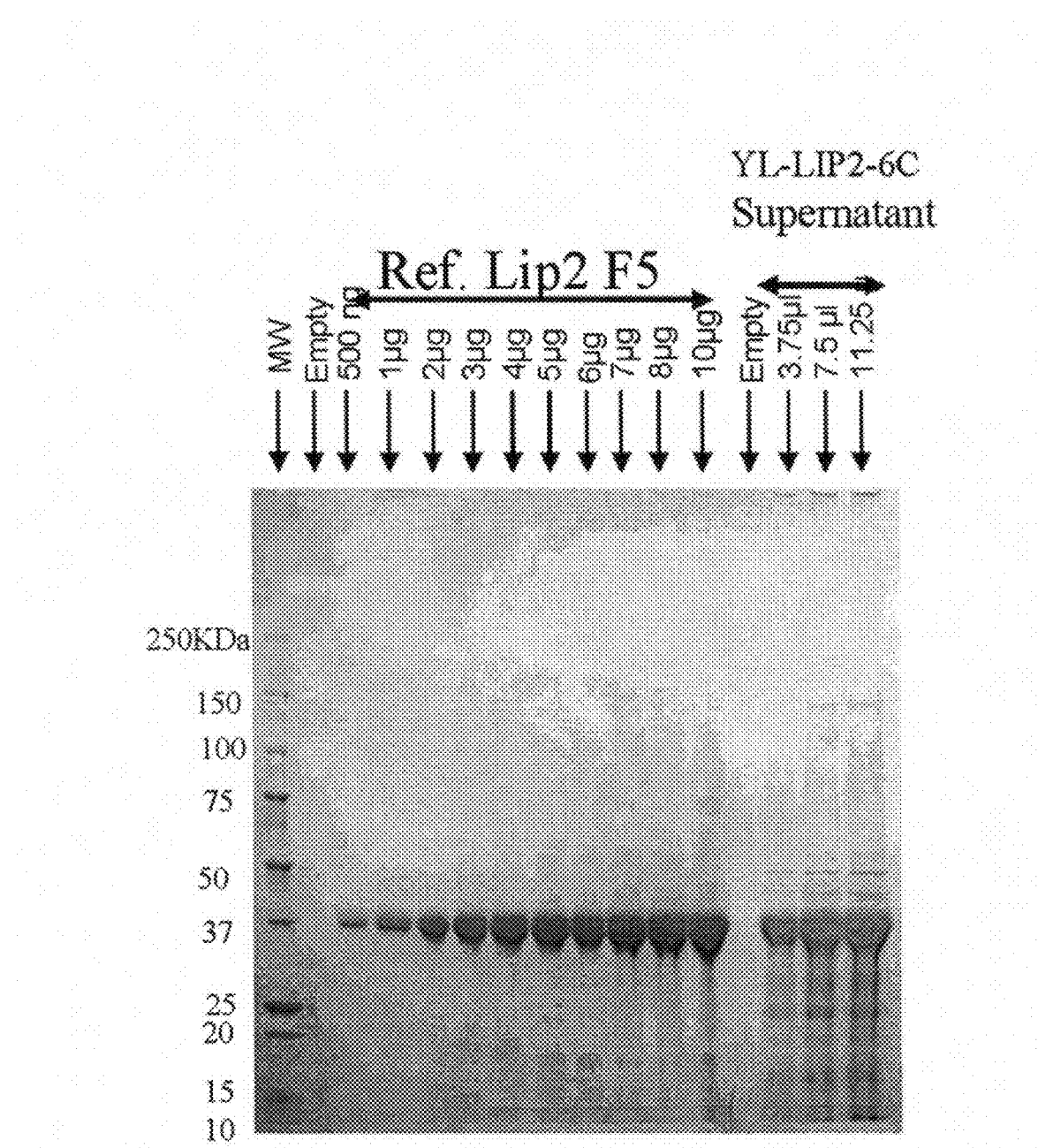

FIG. 5 represents the analysis, by SDS-PAGE, of the purity of the lipase in the supernatant at time T33 (end of the fermentation process). MW: molecular weight ladder; ref. Lip2 F5: Lip2 lipase range from 1 to 10 μg; YL-LIP2-6C supernatant: volumes, in μl, of supernatant analyzed.

Figure 6:
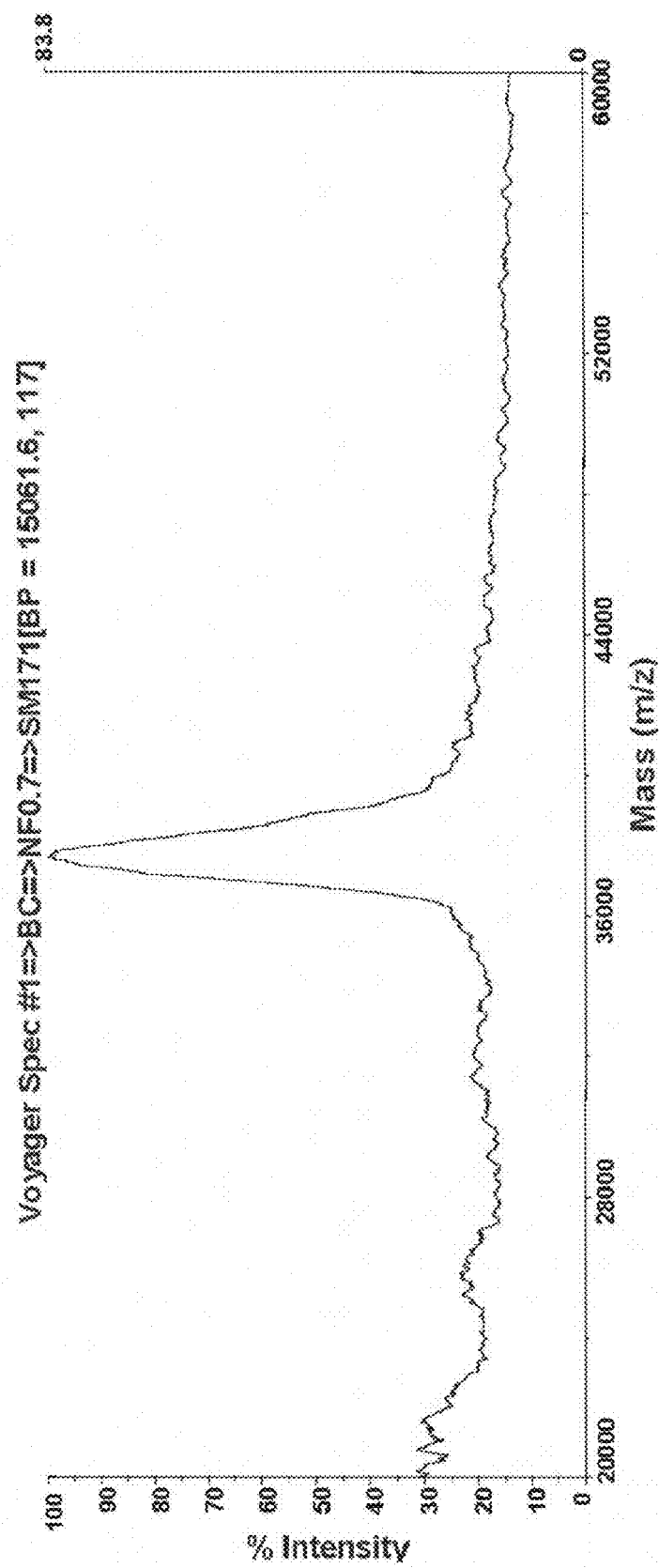

FIG. 6 represents the mass spectrum, determined by MALDI-TOF type mass spectrometry, of the recombinant lipase produced by the YL-LIP2-6C clone.

EXAMPLE 1

Materials and Methods

1) Media Used

The final concentrations indicated are the concentrations in the stock solutions.

Nonenriched Basal Medium 02130S

| Ingredients | Final concentration |
|---|---|
| Glucose | 10 g/l |
| $KH_2PO_4$ | 3 g/l |
| $Na_2HPO_4$ | 3 g/l |
| $H_3BO_3$ | 0.34 g/l |
| $(NH_4)_2SO_4$ | 3 g/l |
| $C_5H_8O_4NNa$ (glutamate) | 1 g/l |
| $MgSO_4$ | 0.5 g/l |
| $CaCl_2$ | 0.023 g/l |
| $MnSO_4$ | 0.038 g/l |
| $ZnSO_4$ | 0.04 g/l |

The Enriched Medium 02130S Additionally Comprises the Following Additives:

| Additives | Final concentration |
|---|---|
| Solution of trace elements | 1 ml/l |
| Solution of vitamins | 1 ml/l |

Composition of the Solution of Trace Elements

| Ingredients | Final concentration |
|---|---|
| $CoCl_2$ | 0.5 g/l |
| $Na_2MoO_4$ | 0.06 g/l |
| $CuSO_4$ | 0.9 g/l |

Composition of the Solution of Vitamins

| Ingredients | Final concentration |
|---|---|
| D-biotin | 0.05 g/l |
| Calcium pantothenate | 1 g/l |
| Nicotinic acid | 1 g/l |
| Myoinositol | 25 g/l |
| Thiamine HCl | 0.25 g/l |
| Pyridoxol HCl | 0.25 g/l |
| p-Aminobenzoic acid | 0.05 g/l |

Composition of the Solution of Inorganic Salts

| Ingredients | Final concentration |
|---|---|
| $MgSO_4$ | 26.76 g/l |
| $CaCl_2$ | 6.40 g/l |
| $FeSO_4$ | 5.61 g/l |
| $CoCl_2$ | 0.29 g/l |
| $ZnSO_4$ | 7.72 g/l |
| $Na_2MoO_4$ | 0.09 g/l |

-continued

| Ingredients | Final concentration |
|---|---|
| H₃BO₃ | 0.34 g/l |
| MnCl₂ | 0.47 g/l |
| CuSO₄ | 0.61 g/l |

Composition of the Solution of FeSO₄

| Ingredients | Final concentration |
|---|---|
| FeSO₄ | 0.9 g/l |

Solution of Ammonia, 14%

Antifoam solution: Struktol J673 diluted 1/10 fold (Schill+Seilacher A G, Moorfleeter Str. 28, 22113, Hamburg, Germany)

2) Extraction of Genomic DNA and Southern Blot Analysis
  a) Extraction of the Genomic DNA The cell pellet obtained from a 4 ml culture is suspended in 0.5 ml of sorbitol buffer (0.9 M sorbitol; 0.1 M tris-HCl, pH=8.0; 0.1 M EDTA). 50 µl of Zymolase® 20T (6 mg/ml) (Euromedex, 67458 Mundolsheim Cedex, France), 50 µl of 2-mercaptoethanol at 0.28 M are added and the solution is incubated for 1 hour at 37° C. with stirring (180 rpm). The solution is subjected to centrifugation and the pellet is suspended in 0.5 ml of TE buffer (50 mM tris-HCl, pH=8; 20 mM EDTA). 50 µl of 10% SDS are added and the solution is mixed by inverting and incubated for 20 min at 65° C. 0.2 ml of 5 M potassium acetate is added, then the solution is mixed and kept in ice for 30 min, and is then centrifuged for 5 min.

The supernatant is transferred to a 1.5 ml tube and then 0.8 ml of 100% ethanol, cooled beforehand in ice, is added. The solution is mixed by inverting and then centrifuged. After removing the supernatant, 0.4 ml of TE buffer containing 100 µg/ml of RNase A (Invitrogen, USA) is added and the solution is incubated for 1 hour at 37° C. After the addition of 1 ml of 100% ethanol, cooled beforehand in ice, the solution is gently mixed until the DNA precipitates, and is then centrifuged. The supernatant is removed and then the DNA pellet is dried in the open air and then suspended in 100 µl of sterile water and then incubated overnight at 4° C.

b) Digestion with the Enzyme HindIII

The concentration of genomic DNA is measured by determining the absorbance at 260 nm ($A_{260}$) and at 280 nm ($A_{280}$). 1 µg of genomic DNA is mixed with sterile water to a final volume of 42.5 µl. 5 µl of buffer (5×) and 2.5 µl of HindIII (50 u/µl) (Invitrogen, USA) are added and the solution is incubated at 37° C. for 4 hours.

c) Southern Blot Analysis

The Southern blot-type transfers are performed following the procedures of the "DIG High Prime DNA Labeling and Detection" kit from the company Roche Diagnostic.

d) Procedure for Labeling of the Probe

The probe corresponding to the entire gene encoding the Lip2 lipase is obtained by PCR performed on the genomic DNA with the aid of the enzyme Phusion DNA polymerase (Finzyme) and the following two primers:

```
                        (SEQ ID NO. 1)
Sense primer:      5'-GTGTACACCTCTACCGAGACCTCT-3'

(SEQ ID NO. 2)
Antisense primer:  5'-TTAGATACCACAGACACCCTCGGT-3'
```

After the PCR reaction, the probe is gel-purified with the aid of the "Nucleospin Extract II" kit (Macherey Nagel). The purified probe is then cold labeled (digoxygenin) with the aid of the "DIG high prime DNA labeling" kit from Roche.

e) Gel-Separation, DNA Transfer and Signal Detection

2 µg of HindIII-digested DNA is mixed with loading buffer and then deposited on a 0.8% agarose gel. The migration is performed at 50 V for 2 h 30 min and then the DNA is transferred on to Hybond+ membrane (Amersham Bioscience). The number of loci of the Lip2 gene in the genomic DNA is detected by means of hybridization, on membranes, of the labeled probe, followed by visualization by exposure to X-rays.

3) Determination of the Protein Concentration

The protein concentration is determined by the Bradford method. The proteins are quantified with the aid of the Bradford method directly on the supernatant of the fermenting culture. The quantity of proteins thus determined is compared with known quantities of purified Lip2 lipase. 20 µl of samples of standards, at the appropriate dilutions, are mixed in tubes with 1 ml of the diluted (5 fold) reagent containing the stain. The $OD_{595}$ is then determined relative to the $OD_{595}$ obtained for the control (dilute stain alone).

4) Measurement of the Specific Activity of the Recombinant Lipase

The activity of the lipase is potentiometrically measured at 37° C. with the aid of a pH-stat device (RADIOMETER). The substrate used is trioctanoin. 10 mM of substrate are emulsified in 15 ml of reaction buffer containing 1 mM tris-HCl (pH 5.5), 150 mM NaCl, 5 mM CaCl₂ and 4 mM sodium taurodeoxycholate (SIGMA). A unit of specific activity is defined as 1 µmol of fatty acid released per minute and per mg of protein.

5) Polyacrylamide Gel Electrophoresis Under Denaturing Conditions (SDS-PAGE)

12 µl of a sample comprising 25% of a mixture containing SDS and reducing agents are loaded on to a 4-12% bistris gel (Biorad). The migration is performed for 45 min at 160 V.

The gel is then analyzed by staining with Coomassie blue.

6) Determination, by Mass Spectrometry of the MALDI-TOF (Matrix-assisted Laser Desorption Ionization-Time of Flight) Type, of the Molecular Mass of the Lip2 Lipase Produced by the YL-LIP2-6C Clone A laser desorption/ionization type mass spectrometry analysis is performed using a "Voyager Elite XL time of flight" mass spectrometer from the company Perseptive Biosystems (Framingham, Mass.) carried out with a nitrogen laser emitting at 337 nm. The mass spectrum in positive mode is obtained using a linear and delayed extraction mode with an acceleration voltage of 25 kV, a grid current of 0.3%, an ion guide current of 0.3%, and a dead time of 1000 ns for the Lip2 protein. Each spectrum is the result of the mean of 100 laser pulses. The material to be analyzed is mixed with an equal volume of a saturated solution of sinapinic acid (Fluka) prepared in a solution containing 50% (v/v) of acetonitrile/aqueous trifluoroacetic acid. 2 µl aliquots of this mixture are deposited on the stainless steel sample plate and are dried in the open air before carrying out the analysis. The external calibration is performed with the aid of alpha-chymotrypsinogen A (Sigma). The expressed values are mean values and correspond to the ion $[M+H]^+$.

EXAMPLE 2

Construction of the Expression Vector and Production of the YL-LIP2-6C Clone

The YL-LIP2-6C strain is obtained by transforming a *Yarrowia lipolytica* strain POld, free of zeta sequences with an expression vector, called JMP6, described in application EP 1 108 043, and comprising the LIP2 gene encoding the Lip2p precursor of the *Yarrowia lipolytica* Lip2 lipase upstream of which is the ACO2 promoter. Said cassette is flanked by zeta sequences, as described above. The construction of the vector JMP6 and the transformation of the POld strain are carried out according to the same procedure as in application EP1108043. This YL-LIP2-6C strain, comprising 5 different loci for integration of the cassette for expression of the LIP2 gene, was deposited at the Collection Nationale de Cultures de Microorganismes (CNCM), 28 rue du Docteur Roux, 75724 Paris Cedex 15, under the number I-3542, on 15 Dec. 2005.

EXAMPLE 3

Figure 1:
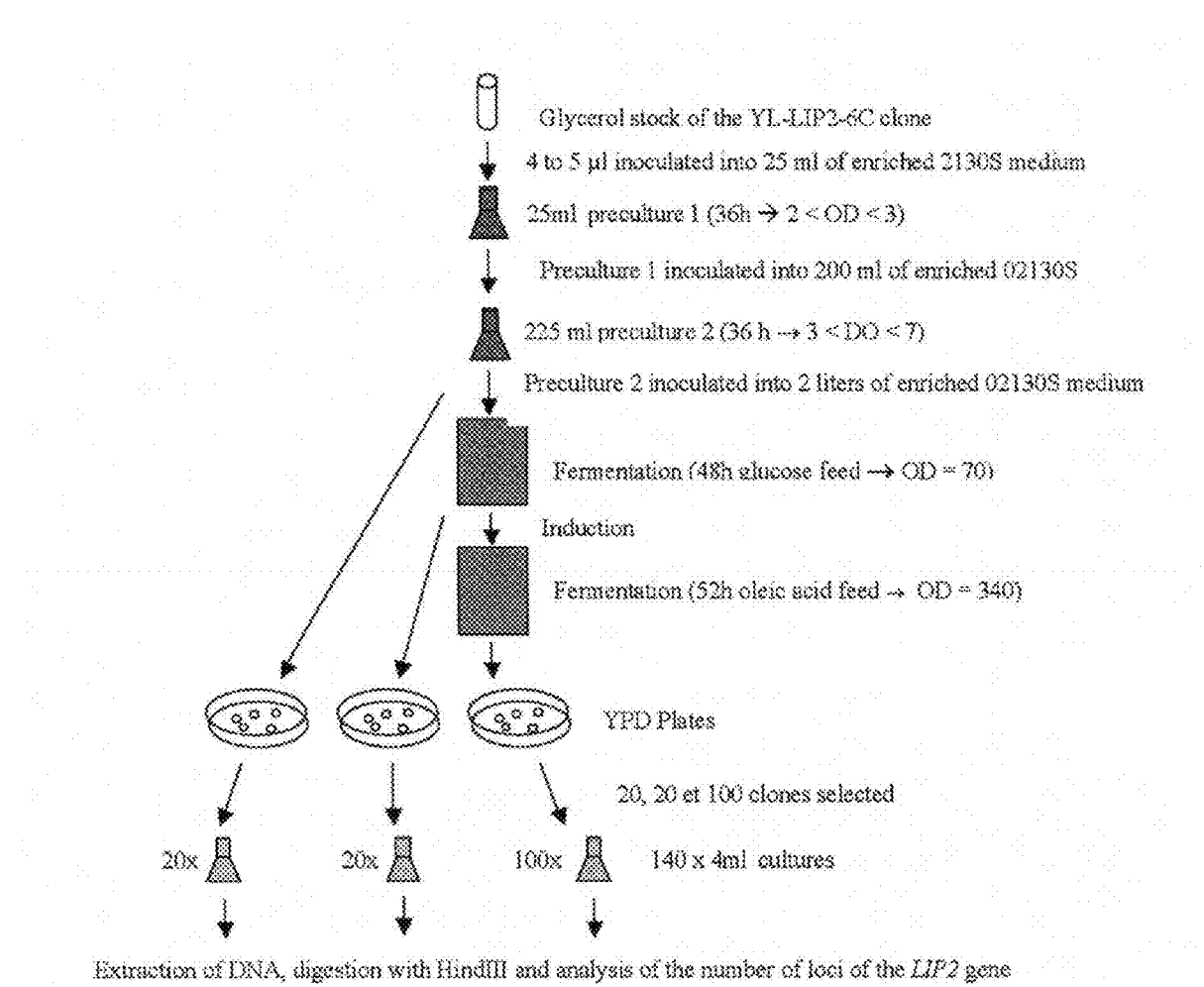
FIG. 1 represents the overall approach for controlling the genetic stability of the YL-LIP2-6C clone during the method for producing lipase.

Production of the Lipase with the YL-LIP2-6C Strain and Verification of the Genetic Stability of YL-LIP2-6C The YL-LIP2-6C strain is used in a method for producing lipase comprising a preculture step and a fermentation step suitable for the production of lipase. The overall approach of this method is illustrated in FIG. 1. The lipase thus produced was then analyzed in terms of activity and quality. Moreover, the genetic stability of YL-LIP2-6C is analyzed by determining the number of loci of the cassette for expressing the LIP2 gene.

1) Method of Production

Precultures and Fermentation

A vial of stock solution of the YL-LIP2-6C clone in glycerol is thawed and 5 μl are cultured in 25 ml of enriched 02130S medium, containing 1% (v/v) of the solution of vitamins and 1% (v/v) of the solution of trace elements, in a 250 ml Erlen Meyer bottle. The culture is incubated at 28° C. for 36 hours with stirring (180 rpm). The resulting preculture of 25 ml (preculture 1) is inoculated into 200 ml of enriched 02130S medium in a 2-liter Erlen Meyer of 2 liters of culture is incubated at 28° C. for 36 hours with stirring (180 rpm). The preculture 2 thus obtained (225 ml) is inoculated in enriched 02130S medium in a fermenter.

At time T0 of the fermentation process, 2 ml of the $FeSO_4$ solution are added to the culture. Every 6 to 9 hours, 2 to 3 ml of the vitamin solution are added to the fermenting culture and after 34 hours of fermentation (at T12), the supply of glucose is initiated. The glucose supply is gradually increased for 14 hours and then interrupted at T17 (corresponding to 48 hours of fermentation) and the induction with oleic acid is then initiated. The supply of oleic acid is gradually increased for the next 54 hours, and then at T33 (102 hours of fermentation) an $OD_{600}$ of 340 is reached and the fermentation process is stopped. The final 3-liter culture is centrifuged (14 000 rpm). The supernatant is recovered and stored at −20° C.

Monitoring of the Cultures

Figure 2:
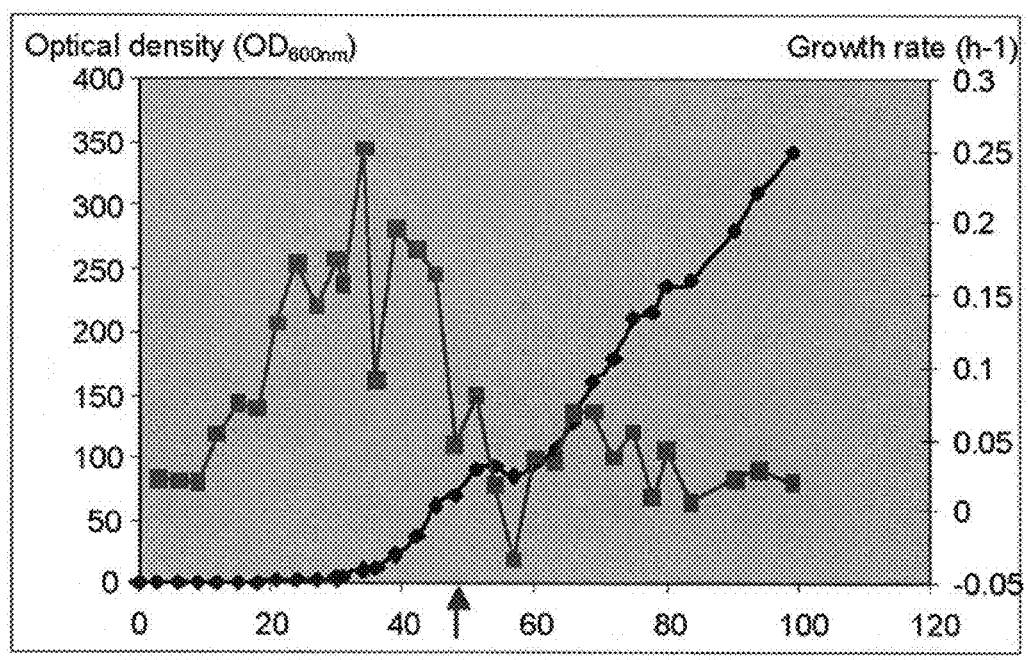
FIG. 2 represents the variation of the optical density at 600 nm ($OD_{600nm}$, y axis left) (-♦-) and the variation of the growth rate ($h^{-1}$, y axis right) (-■-) as a function of time (hours, x axis) during the fermentation process. The arrow indicates the induction of the production of lipase.

During the fermentation, the temperature, the oxygen partial pressure and the pH are monitored and maintained at 28° C., 20% and 6.2, respectively. Every 3 hours approximately, a culture sample is collected and the $OD_{600}$ is measured in order to monitor the variation of the growth rate. The results are indicated in FIG. 2. Two 1 ml extracts of these samples are centrifuged for 5 min at 14 000 rpm and the pellets and supernatants are stored at −20° C. Table I shows the monitoring of the fermentation process.

TABLE I

Monitoring of the fermentation process

| T | Time of fermentation/ hours | OD600 | Growth rate (h-1) | Vitamins added: 2 ml every 12 h | Stirring (rpm) | PO2 (%) | pH | Other actions and remarks | Temp. (° C.) |
|---|---|---|---|---|---|---|---|---|---|
| T0 | 0.00 | 0.28 | | 2 ml | 300 | 98 | 6.21 | 2 ml $FeSO_4$ | 28 |
| T1 | 3.00 | 0.3 | 0.02299762 | | 300 | 98 | 6.47 | | 28 |
| T2 | 6.00 | 0.32 | 0.02151284 | | 300 | 98 | 6.51 | | 28 |
| T3 | 9.00 | 0.34 | 0.02020821 | | 300 | 98 | 6.53 | | 28 |
| T4 | 12.00 | 0.4 | 0.05417298 | 2 ml | 300 | 100 | 6.57 | | 28 |
| T5 | 15.00 | 0.5 | 0.07438118 | | 300 | 98 | 6.2 | pH adjustment with orthophosphoric acid | 28 |
| T6 | 18.00 | 0.62 | 0.07170379 | | 300 | 97 | 6.2 | | 28 |
| T7 | 21.00 | 0.92 | 0.1315514 | 2 ml | 300 | 92.7 | 6.19 | | 28 |
| T8 | 24.00 | 1.54 | 0.17172134 | | 300 | 80.9 | 6.2 | | 28 |
| T9 | 27.00 | 2.36 | 0.14229307 | | 300 | 61.4 | 6.19 | | 28 |
| T10 | 30.00 | 3.99 | 0.1750432 | 2 ml | 300 | 20 | 6.19 | | 28 |
| T11 | 31.00 | 4.67 | 0.15736784 | | 331 | 20 | 6.2 | Problem with glucose feed | 28 |
| T12 | 34.00 | 9.97 | 0.25280717 | | 392 | 20.6 | 6.2 | Start glucose feed | 28 |
| T13 | 36.00 | 11.96 | 0.09099358 | 2 ml | 378 | 17.6 | 6.2 | | 28 |
| T14 | 39.00 | 21.5 | 0.19549506 | | 401 | 19.7 | 6.23 | | 28 |
| T15 | 42.00 | 37.2 | 0.18275194 | | 424 | 18.9 | 6.2 | | 28 |
| T16 | 45.00 | 61 | 0.16485503 | | 445 | 20 | 6.2 | | 28 |
| T17 | 48.00 | 70 | 0.04587379 | 2 ml | 470 | 20 | 6.4 | Induction oleic acid | 28 |
| T18 | 51.00 | 89 | 0.08004704 | | 366 | 20 | 6.38 | | 28 |
| T19 | 54.00 | 93.86 | 0.01772265 | | 409 | 20.3 | 6.17 | | 28 |
| T20 | 57.00 | 85 | −0.03305102 | | 535 | 19.5 | 6.19 | | 28 |
| T21 | 60.00 | 95 | 0.03707521 | 3 ml | 615 | 20.2 | 6.21 | | 28 |
| T22 | 63.00 | 105 | 0.03336115 | | 563 | 21.5 | 6.2 | | 28 |
| T23 | 66.00 | 129 | 0.06861735 | | 583 | 20.4 | 6.2 | | 28 |
| T24 | 69.00 | 159 | 0.06969727 | | 580 | 21.2 | 6.18 | | 28 |
| T25 | 72.00 | 178 | 0.03762645 | 3 ml | 563 | 19 | 6.18 | | 28 |
| T26 | 75.00 | 210 | 0.05510799 | | 565 | 19.5 | 6.2 | | 28 |
| T27 | 78.00 | 216 | 0.09939029 | | 589 | 20 | 6.2 | | 28 |
| T28 | 80.00 | 235 | 0.04215355 | | 590 | 20 | 6.2 | | 28 |
| T29 | 83.50 | 240 | 0.00601526 | 3 ml | 610 | 20 | 6.2 | | 28 |
| T30 | 90.50 | 280 | 0.02202153 | | 640 | 21 | 6.2 | | 28 |
| T31 | 94.00 | 310 | 0.02908077 | | 687 | 19.5 | 6.19 | | 28 |
| T32 | 99.00 | 342 | 0.01964769 | | 691 | 20 | 6.19 | | 28 |
| T33 | 100 | 340 | −0.00586512 | | 680 | 20 | 6.2 | | 28 |

Purification of the Lipase

Optionally, an additional step for purifying the lipase is carried out.

The lipase is separated from the culture with the aid of a tangential microfiltration device on a ceramic membrane (pilot X6 from PALL) allowing the retention of yeasts with a size greater than the cut-off (0.1 μm). The permeate containing the lipase is recovered first in concentration mode, and then in diafiltration mode. These steps are carried out according to the recommendation of the manufacturer with appropriate modifications. The concentration of microorganisms contained in the permeate is then reduced by filtration (0.2 μm) (Millipore) so as to obtain a bioload of less than 10 cfu/ml. Using a Profux M12 device (Millipore), the lipase solution is concentrated, to a volume of about 5 liters, and subjected to tangential ultrafiltration using a Biomax 10 kDa standard Pellicon membrane in order to remove the contaminants of low molecular weight. The ultrafiltrate, containing no lipase, is removed. The lipase solution is then again purified by removing microorganisms, as indicated above, so as to obtain a bioload of less than 5 cfu/ml. The lipase thus purified may be additionally subjected to freeze-drying.

3) Characterization of the Recombinant Lipase Produced by YL-LIP2-6C a) Monitoring of the Production of Lipase by the YL-LIP2-6C Strain During the Fermentation Process At each measurement point, a culture sample is subjected to centrifugation and the supernatant is analyzed by SDS-PAGE. 75 μl of the supernatant are mixed with 75 μl of water and then 5 μl are loaded on a 26-well gel. Samples containing known quantities of Lip2 lipase are also analyzed. The results are illustrated in FIG. 4. By comparing the quantity of lipase obtained at the end of fermentation (T33), with the gradient of known quantities of Lip2 lipase, the concentration of lipase obtained after 100 hours of fermentation may be estimated at 1.5 g/l.

Moreover, the inventors used the method for producing lipase according to the invention for a final volume of about 35 liters, which allowed the production of lipase in a yield between 1 and 3 g per liter of culture supernatant.

b) Determination of the Protein Concentration and Estimation of the Yield of Production of Recombinant Lipase The protein concentration in the culture supernatant is determined as indicated in example 1 (Bradford method). Seven independent measures are performed and the protein concentration in the supernatant is 2.3 g/l. The purity of the Lip2 protein in the supernatant is estimated by SDS-PAGE. The results are illustrated in FIG. 5. The degree of purity is estimated at about 70%. The resulting yield of production of lipase from the fermentation step with the YL-LIP2-6C clone is therefore 1.6 g/l.

c) Measurement of the Specific Activity of the Recombinant Lipase Produced by YL-LIP2-6C The specific activity of the lipase produced by the YL-LIP2-6C clone is measured as indicated in example 1. The sample corresponding to the fermentation supernatant is diluted 100 fold in a buffer containing 50 mM of $Na_2HPO_4$, 50 mM of $KH_2PO_4$, 150 mM of NaCl, pH 6.0. The catalytic activity determined at 37° C. with trioctanoin on 3 independent experiments is 21 883.33 U/ml of the supernatant (table II).

TABLE II

Measurement of the activity of samples of the fermentation supernatant

| | Lipase activity (U/ml) | | | | |
|---|---|---|---|---|---|
| | Trials | | | Mean | SD |
| Sample | 20 800.00 | 22 750.00 | 22 100.00 | 21 883.33 | 992.89 |

From the estimated concentration of Lip2 lipase in the supernatant (see above), the specific activity of the lipase is 13 675 U/mg, comparable to the specific activity of the lipase produced for the clinical studies. The specific activity of the lipase produced by the YL-LIP2-6C clone is in conformity with the conditions required for the clinical batches.

d) Molecular Mass of the Recombinant Lipase

The mass spectrum analysis (see example 1) is performed on the fermentation culture supernatant after centrifugation without purification. The result is illustrated in FIG. 6. The major peak observed reveals a molecular mass of 37 648 Da. The Lip2 lipase produced by YL-LIP2-6C has a reasonable molecular mass because the observed value is in conformity with the conditions required for the clinical batches, that is to say 37 500+/−1000 Da.

This example illustrates the selection of a stable clone, YL-LIP2-6C (in this case, 100% of the clones analyzed after 30 generations have the same number of loci of the Lip2 gene as the initial clone). In addition, the genetic stability of said clone is not affected by the culture conditions used for the production of lipase (during the precultures; just before the fermentation; just before the induction by oleic acid of the production of lipase; at the end of the fermentation).

3) Genetic Stability of the YL-LIP2-6C Clone

The genetic stability of the YL-LIP2-6C clone during the method for producing lipase, comprising a preculture step and a fermentation step, is analyzed by determining the number of events for integration of the cassette for expressing the LIP2 gene at different loci in the *Yarrowia lipolytica* DNA, in the colonies selected at T0, T17 and T33.

a) Selection of the Colonies

A sample of the preculture 2 (T0, initiation of the fermentation), a sample of the culture under fermentation conditions at T17 (just before the induction) and at T33 (end of the fermentation) are diluted, in a first instance up to an $OD_{600}=1$, and are then diluted 1000 fold. 10 μl of these dilute solutions are each spread on 3 culture plates on YPD medium. The plates are then incubated at 28° C. for 48 hours and are then stored at 4° C. up to the selection of colonies for the analysis of the number of loci.

20 colonies derived from the sample collected at the starting point of the fermentation (T0), 20 colonies derived from the sample collected just before the induction (T17) and 100 colonies derived from the sample collected at the end of fermentation (T33) are separately inoculated in 4 ml of enriched 02130S medium and then cultured for 72 hours. Next, stocks in 30% glycerol are prepared for the extraction of DNA and the Southern blot analysis (Materials and Methods).

b) Determination of the Number of Events for Integration of the LIP2 Gene at Different Loci for 140 Colonies Derived from the YL-LIP2-6C Strain The results of the Southern blot analysis of the number of events for integration at different loci of the LIP2 gene on 20 colonies collected at time T0 (start of fermentation), 20 colonies collected at time T17 (48 hours of fermentation) and 100 colonies collected at time T33 (100 hours of fermentation) are illustrated in FIG. 3. These results show that all the colonies analyzed contain 6 loci of the LIP2 gene. Since the wild-type strain contains a copy of the endogenous LIP2 gene, the YL-LIP2-6C strain therefore contains 5 loci for integration of the cassette for expression of the LIP2 gene. The YL-LIP2-6C clone is therefore 100% stable during a 100 hour fermentation process.

The invention claimed is:

1. A preparation of yeast acid-resistant recombinant lipase LIP2, obtained by a method comprising:
   a) culturing *Yarrowia lipolytica* cells transformed with a vector comprising a cassette for expressing a yeast acid-resistant lipase LIP2 are cultured, and
   b) recovering a recombinant lipase LIP2 produced by said cells from the culture supernatant,
   wherein the culturing is carried out in a culture medium free of products of animal origin or of uncharacterized mixtures consisting of protein materials of animal origin or of products of their enzymatic digestion, and
   said preparation has a catalytic activity at pH 6 of at least 15 000 units per ml of culture supernatant, one unit corresponding to the quantity of enzyme capable of catalyzing the release of 1 µmol of fatty acid per minute when the substrate used is trioctanoin, and/or in that the concentration of said lipase in said preparation is greater than 1 g of lipase per liter,
   wherein said *Yarrowia lipolytica* cell is the clone YL-LIP2-6C, deposited at the Collection Nationale de Cultures de Microorganismes (C.N.C.M.), 28 rue du Docteur Roux, 75724 Paris Cedex 15, under the number I-3542, on 15 Dec. 2005.

2. The preparation as claimed in claim 1, which has a catalytic activity at pH 6 of at least 20 000 units per ml of culture supernatant, one unit corresponding to the quantity of enzyme capable of catalyzing the release of 1 µmol of fatty acid per minute when the substrate used is trioctanoin.

3. A medicament comprising a lipase preparation as claimed in claim 1.

4. A method for the treatment of a fat malabsorption syndrome linked to a pancreatic insufficiency comprising administration of a lipase preparation according to claim 1 to a subject in need thereof.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1
gtgtacacct ctaccgagac ctct                                    24

<210> SEQ ID NO 2
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 2
ttagatacca cagacaccct cggt                                    24